(12) United States Patent
Govari et al.

(10) Patent No.: US 9,326,700 B2
(45) Date of Patent: *May 3, 2016

(54) CATHETER DISPLAY SHOWING TIP ANGLE AND PRESSURE

(75) Inventors: Assaf Govari, Haifa (IL); Yaron Ephrath, Karkur (IL); Andres Claudio Altmann, Haifa (IL); Nahum Kilim, Haifa (IL)

(73) Assignee: Biosense Webster (Israel) Ltd. (IL)

( * ) Notice: Subject to any disclaimer, the term of this patent is extended or adjusted under 35 U.S.C. 154(b) by 1308 days.

This patent is subject to a terminal disclaimer.

(21) Appl. No.: 12/342,747

(22) Filed: Dec. 23, 2008

(65) Prior Publication Data

US 2010/0160770 A1    Jun. 24, 2010

(51) Int. Cl.
| A61B 18/14 | (2006.01) |
| A61B 5/05 | (2006.01) |
| A61B 5/06 | (2006.01) |
| A61B 5/00 | (2006.01) |
| A61B 19/00 | (2006.01) |

(52) U.S. Cl.
CPC .............. *A61B 5/06* (2013.01); *A61B 5/6885* (2013.01); *A61B 2019/5251* (2013.01)

(58) Field of Classification Search
CPC ............. A61B 2019/5251; A61B 5/6885; A61B 5/06
USPC ................................... 600/434, 423
See application file for complete search history.

(56) References Cited

U.S. PATENT DOCUMENTS

| 3,841,150 A | 10/1974 | Pearson |
| 3,971,364 A | 7/1976 | Fletcher et al. |
| 4,764,114 A | 8/1988 | Jeffcoat et al. |
| 4,856,993 A | 8/1989 | Maness et al. |
| 4,930,494 A | 6/1990 | Takehana et al. |
| 5,263,493 A | 11/1993 | Avitall |
| 5,368,564 A | 11/1994 | Savage |
| 5,391,199 A | 2/1995 | Ben-Haim |
| 5,462,527 A | 10/1995 | Stevens-Wright et al. |
| 5,487,757 A | 1/1996 | Truckai et al. |
| 5,499,542 A | 3/1996 | Morlan |
| 5,542,434 A | 8/1996 | Imran et al. |

(Continued)

FOREIGN PATENT DOCUMENTS

| DE | 19750441 A | 6/1999 |
| EP | 928601 A1 | 7/1999 |

(Continued)

OTHER PUBLICATIONS

Kanagaratnam, Prapa et al. Experience of robotic catheter ablation in humans using novel remotely steerable catheter sheath. Journal of Interventional Cardiac Electrophysiology. vol. 21, No. 1, p. 19-26 (2008).*

(Continued)

*Primary Examiner* — Long V Le
*Assistant Examiner* — Helene Bor

(57) ABSTRACT

A method for displaying information includes receiving a measurement with respect to an invasive probe inside a body of a subject of at least one probe parameter, selected from a group of parameters consisting of a bend angle of the probe and a pressure on the probe. Responsively to the measurement, an icon is displayed on a display screen representing the at least one probe parameter for viewing by an operator of the probe.

12 Claims, 2 Drawing Sheets

(56) References Cited

U.S. PATENT DOCUMENTS

| | | |
|---|---|---|
| 5,558,091 A | 9/1996 | Acker et al. |
| 5,563,354 A | 10/1996 | Kropp |
| 5,662,124 A | 9/1997 | Wilk |
| 5,673,695 A | 10/1997 | McGee et al. |
| 5,680,860 A | 10/1997 | Imran |
| 5,685,878 A | 11/1997 | Falwell et al. |
| 5,728,149 A | 3/1998 | Laske et al. |
| 5,769,843 A * | 6/1998 | Abela et al. ............... 606/10 |
| 5,826,576 A | 10/1998 | West |
| 5,833,608 A | 11/1998 | Acker |
| 5,836,894 A | 11/1998 | Sarvazyan |
| 5,860,974 A | 1/1999 | Abele |
| 5,861,024 A | 1/1999 | Rashidi |
| 5,902,248 A | 5/1999 | Millar et al. |
| 5,916,147 A | 6/1999 | Boury |
| 5,944,022 A | 8/1999 | Nardella et al. |
| 5,947,320 A | 9/1999 | Bordner et al. |
| 5,964,757 A | 10/1999 | Ponzi |
| 5,974,320 A | 10/1999 | Ward et al. |
| 5,983,126 A | 11/1999 | Wittkampf |
| 6,048,329 A | 4/2000 | Thompson et al. |
| 6,063,022 A | 5/2000 | Ben-Haim |
| 6,123,699 A | 9/2000 | Webster, Jr. |
| 6,171,277 B1 | 1/2001 | Ponzi |
| 6,177,792 B1 | 1/2001 | Govari et al. |
| 6,183,463 B1 | 2/2001 | Webster, Jr. |
| 6,198,974 B1 | 3/2001 | Webster, Jr. |
| 6,201,387 B1 | 3/2001 | Govari |
| 6,203,493 B1 | 3/2001 | Ben-Haim |
| 6,216,027 B1 | 4/2001 | Willis et al. |
| 6,226,542 B1 | 5/2001 | Reisfeld |
| 6,239,724 B1 | 5/2001 | Doron et al. |
| 6,241,724 B1 | 6/2001 | Fleischman et al. |
| 6,266,551 B1 | 7/2001 | Osadchy et al. |
| 6,272,371 B1 * | 8/2001 | Shlomo ............... 600/424 |
| 6,272,672 B1 | 8/2001 | Conway |
| 6,301,496 B1 | 10/2001 | Reisfeld |
| 6,332,089 B1 | 12/2001 | Acker et al. |
| 6,334,837 B1 | 1/2002 | Hein |
| 6,335,617 B1 | 1/2002 | Osadchy et al. |
| 6,351,549 B1 | 2/2002 | Souluer |
| 6,398,738 B1 | 6/2002 | Millar |
| 6,436,059 B1 | 8/2002 | Zanelli |
| 6,456,864 B1 | 9/2002 | Swanson et al. |
| 6,484,118 B1 | 11/2002 | Govari |
| 6,551,302 B1 | 4/2003 | Rosinko et al. |
| 6,569,098 B2 | 5/2003 | Kawchuk |
| 6,574,492 B1 | 6/2003 | Ben-Haim et al. |
| 6,584,856 B1 | 7/2003 | Biter et al. |
| 6,602,242 B1 | 8/2003 | Fung et al. |
| 6,612,992 B1 | 9/2003 | Hossack et al. |
| 6,618,612 B1 | 9/2003 | Acker et al. |
| 6,690,963 B2 | 2/2004 | Ben-Haim et al. |
| 6,695,808 B2 | 2/2004 | Tom |
| 6,711,429 B1 | 3/2004 | Gilboa et al. |
| 6,727,371 B2 | 4/2004 | Müller et al. |
| 6,814,733 B2 | 11/2004 | Schwartz et al. |
| 6,835,173 B2 | 12/2004 | Couvillon, Jr. |
| 6,892,091 B1 | 5/2005 | Ben-Haim et al. |
| 6,915,149 B2 | 7/2005 | Ben-Haim |
| 6,945,956 B2 | 9/2005 | Waldhauser et al. |
| 6,964,205 B2 | 11/2005 | Papakostas et al. |
| 6,973,339 B2 | 12/2005 | Govari |
| 6,997,924 B2 | 2/2006 | Schwartz et al. |
| 7,077,823 B2 | 7/2006 | McDaniel |
| 7,156,816 B2 | 1/2007 | Schwartz et al. |
| 7,235,070 B2 | 6/2007 | Vanney |
| 7,297,116 B2 | 11/2007 | Varghese et al. |
| 7,306,593 B2 | 12/2007 | Keidar et al. |
| 7,306,599 B2 | 12/2007 | Karasawa et al. |
| 7,311,704 B2 | 12/2007 | Paul et al. |
| 7,397,364 B2 | 7/2008 | Govari |
| 7,435,232 B2 | 10/2008 | Liebschner |
| 7,465,288 B2 | 12/2008 | Dudney et al. |
| 7,481,774 B2 | 1/2009 | Brockway et al. |
| 7,536,218 B2 | 5/2009 | Govari et al. |
| 7,604,605 B2 | 10/2009 | Zvuloni |
| 7,662,151 B2 | 2/2010 | Crompton, Jr. et al. |
| 7,681,432 B2 | 3/2010 | Hay et al. |
| 7,686,767 B2 | 3/2010 | Maschke |
| 7,911,315 B2 | 3/2011 | Bradley |
| 7,914,440 B2 | 3/2011 | Otawara |
| 7,959,601 B2 | 6/2011 | McDaniel et al. |
| 7,984,659 B2 | 7/2011 | Fujimoto et al. |
| 8,043,216 B2 | 10/2011 | Matsumura |
| 8,046,049 B2 | 10/2011 | Govari et al. |
| 8,083,691 B2 | 12/2011 | Goldenberg et al. |
| 8,137,275 B2 | 3/2012 | Fan et al. |
| 8,357,152 B2 | 1/2013 | Govari et al. |
| 8,374,819 B2 | 2/2013 | Govari et al. |
| 8,535,308 B2 | 9/2013 | Govari et al. |
| 8,900,229 B2 | 12/2014 | Govari et al. |
| 8,926,528 B2 | 1/2015 | Govari et al. |
| 9,033,916 B2 | 5/2015 | Schultz |
| 2001/0047129 A1 * | 11/2001 | Hall et al. ............... 600/374 |
| 2001/0047133 A1 | 11/2001 | Gilboa et al. |
| 2002/0002329 A1 | 1/2002 | Avitall |
| 2002/0065455 A1 | 5/2002 | Ben-Haim et al. |
| 2002/0068866 A1 | 6/2002 | Zikorus et al. |
| 2002/0068931 A1 | 6/2002 | Wong et al. |
| 2002/0087089 A1 | 7/2002 | Ben-Haim |
| 2002/0165461 A1 | 11/2002 | Hayzelden et al. |
| 2002/0193781 A1 | 12/2002 | Loeb |
| 2003/0120150 A1 | 6/2003 | Govari |
| 2003/0120195 A1 | 6/2003 | Milo et al. |
| 2003/0130615 A1 | 7/2003 | Tom |
| 2003/0158494 A1 | 8/2003 | Dahl et al. |
| 2003/0187389 A1 | 10/2003 | Morency et al. |
| 2004/0049255 A1 | 3/2004 | Jain et al. |
| 2004/0064024 A1 | 4/2004 | Sommer |
| 2004/0068178 A1 | 4/2004 | Govari |
| 2004/0097806 A1 * | 5/2004 | Hunter et al. ............... 600/434 |
| 2004/0102769 A1 | 5/2004 | Schwartz et al. |
| 2004/0147920 A1 | 7/2004 | Keidar |
| 2004/0244464 A1 | 12/2004 | Hajdukiewicz et al. |
| 2004/0254458 A1 | 12/2004 | Govari |
| 2005/0033135 A1 | 2/2005 | Govari |
| 2005/0080429 A1 | 4/2005 | Freyman et al. |
| 2005/0096590 A1 | 5/2005 | Gullickson et al. |
| 2005/0228274 A1 | 10/2005 | Boese et al. |
| 2005/0277875 A1 | 12/2005 | Selkee |
| 2006/0009690 A1 | 1/2006 | Fuimaono et al. |
| 2006/0009735 A1 | 1/2006 | Viswanathan et al. |
| 2006/0015096 A1 | 1/2006 | Hauck et al. |
| 2006/0064038 A1 | 3/2006 | Omata et al. |
| 2006/0074297 A1 | 4/2006 | Viswanathan |
| 2006/0173480 A1 | 8/2006 | Zhang |
| 2006/0184106 A1 | 8/2006 | McDaniel et al. |
| 2006/0200049 A1 | 9/2006 | Leo et al. |
| 2006/0247618 A1 | 11/2006 | Kaplan et al. |
| 2006/0276703 A1 | 12/2006 | Fuimaono et al. |
| 2007/0021742 A1 | 1/2007 | Viswanathan |
| 2007/0060832 A1 | 3/2007 | Levin |
| 2007/0060847 A1 | 3/2007 | Leo et al. |
| 2007/0100332 A1 | 5/2007 | Paul et al. |
| 2007/0106114 A1 | 5/2007 | Sugimoto et al. |
| 2007/0106165 A1 | 5/2007 | Tulkki |
| 2007/0142749 A1 | 6/2007 | Khatib et al. |
| 2007/0151391 A1 | 7/2007 | Larkin et al. |
| 2007/0156114 A1 | 7/2007 | Worley et al. |
| 2007/0161882 A1 | 7/2007 | Pappone |
| 2007/0167740 A1 | 7/2007 | Grunewald et al. |
| 2007/0167804 A1 | 7/2007 | Park et al. |
| 2007/0167818 A1 | 7/2007 | Osborn et al. |
| 2007/0167819 A1 | 7/2007 | Osborn et al. |
| 2007/0179492 A1 | 8/2007 | Pappone |
| 2007/0185397 A1 | 8/2007 | Govari et al. |
| 2007/0191829 A1 | 8/2007 | McGee et al. |
| 2007/0197939 A1 * | 8/2007 | Wallace et al. ............... 600/587 |
| 2007/0233044 A1 | 10/2007 | Wallace et al. |
| 2007/0282211 A1 | 12/2007 | Ofek et al. |
| 2008/0009750 A1 | 1/2008 | Aeby et al. |
| 2008/0015568 A1 | 1/2008 | Paul et al. |
| 2008/0051704 A1 | 2/2008 | Patel et al. |

(56) References Cited

U.S. PATENT DOCUMENTS

| | | |
|---|---|---|
| 2008/0065111 A1 | 3/2008 | Blumenkranz et al. |
| 2008/0071267 A1 | 3/2008 | Wang et al. |
| 2008/0077049 A1 | 3/2008 | Hirshman |
| 2008/0146918 A1 | 6/2008 | Magnin et al. |
| 2008/0161796 A1 | 7/2008 | Cao et al. |
| 2008/0183075 A1 | 7/2008 | Govari et al. |
| 2008/0200843 A1 | 8/2008 | Williams et al. |
| 2008/0249467 A1 | 10/2008 | Burnett et al. |
| 2008/0249522 A1 | 10/2008 | Pappone et al. |
| 2008/0255540 A1 | 10/2008 | Selkee |
| 2008/0269606 A1 | 10/2008 | Matsumura |
| 2008/0275428 A1 | 11/2008 | Tegg et al. |
| 2008/0275442 A1 | 11/2008 | Paul et al. |
| 2008/0275465 A1 | 11/2008 | Paul et al. |
| 2008/0281319 A1 | 11/2008 | Paul et al. |
| 2008/0287777 A1 | 11/2008 | Li et al. |
| 2008/0288038 A1 | 11/2008 | Paul et al. |
| 2008/0294144 A1 | 11/2008 | Leo et al. |
| 2008/0294158 A1 | 11/2008 | Pappone et al. |
| 2009/0010021 A1 | 1/2009 | Smith et al. |
| 2009/0093806 A1 | 4/2009 | Govari et al. |
| 2009/0138007 A1 | 5/2009 | Govari et al. |
| 2009/0158511 A1 | 6/2009 | Maze et al. |
| 2009/0177111 A1 | 7/2009 | Miller et al. |
| 2009/0275966 A1 | 11/2009 | Mitusina |
| 2009/0287118 A1 | 11/2009 | Malek |
| 2009/0294361 A1 | 12/2009 | Larsen |
| 2009/0306515 A1 | 12/2009 | Matsumura |
| 2009/0306650 A1 | 12/2009 | Govari et al. |
| 2010/0063478 A1 | 3/2010 | Selkee |
| 2010/0069921 A1 | 3/2010 | Miller et al. |
| 2010/0121138 A1 | 5/2010 | Goldenberg et al. |
| 2010/0137845 A1 | 6/2010 | Ramstein et al. |
| 2010/0152574 A1 | 6/2010 | Erdman et al. |
| 2010/0160770 A1 | 6/2010 | Govari et al. |
| 2010/0160778 A1 | 6/2010 | Eskandari et al. |
| 2010/0168620 A1 | 7/2010 | Klimovitch et al. |
| 2010/0168918 A1 | 7/2010 | Zhao et al. |
| 2010/0292566 A1 | 11/2010 | Nagano et al. |
| 2010/0298826 A1 | 11/2010 | Leo et al. |
| 2011/0054354 A1 | 3/2011 | Hunter et al. |
| 2011/0054355 A1 | 3/2011 | Hunter et al. |
| 2011/0071436 A1 | 3/2011 | Althoefer et al. |
| 2011/0130648 A1 | 6/2011 | Beeckler et al. |
| 2011/0152880 A1 | 6/2011 | Alvarez et al. |
| 2011/0153252 A1 | 6/2011 | Govari et al. |
| 2011/0153253 A1 | 6/2011 | Govari et al. |
| 2011/0160556 A1 | 6/2011 | Govari |
| 2011/0172538 A1 | 7/2011 | Sumi |
| 2011/0184406 A1 | 7/2011 | Selkee |
| 2011/0307207 A1 | 12/2011 | Govari et al. |
| 2012/0004576 A1 | 1/2012 | Govari et al. |
| 2012/0041295 A1 | 2/2012 | Schultz |
| 2012/0089358 A1 | 4/2012 | Ludwin et al. |
| 2012/0108988 A1 | 5/2012 | Ludwin et al. |
| 2012/0149966 A1 | 6/2012 | Ludwin et al. |
| 2012/0149967 A1 | 6/2012 | Ludwin et al. |
| 2012/0150075 A1 | 6/2012 | Ludwin et al. |
| 2012/0184864 A1 | 7/2012 | Harlev et al. |
| 2012/0184865 A1 | 7/2012 | Harlev et al. |
| 2012/0253167 A1 | 10/2012 | Bonyak et al. |
| 2012/0259194 A1 | 10/2012 | Selkee |
| 2012/0271145 A1 | 10/2012 | Govari et al. |
| 2012/0310116 A1 | 12/2012 | Ludwin et al. |
| 2012/0316407 A1 | 12/2012 | Anthony et al. |
| 2013/0018306 A1 | 1/2013 | Ludwin |

FOREIGN PATENT DOCUMENTS

| | | |
|---|---|---|
| EP | 980693 A1 | 2/2000 |
| EP | 1502555 A1 | 2/2005 |
| EP | 1586281 A1 | 10/2005 |
| EP | 1690564 A1 | 8/2006 |
| EP | 1743575 A2 | 1/2007 |
| EP | 1820464 A1 | 8/2007 |
| EP | 1897581 A2 | 3/2008 |
| EP | 2 000 789 A2 | 12/2008 |
| EP | 2 047 797 A2 | 4/2009 |
| EP | 2127604 A1 | 12/2009 |
| EP | 2130508 B1 | 12/2009 |
| EP | 2196143 A1 | 6/2010 |
| EP | 2305115 A1 | 4/2011 |
| EP | 2338412 A1 | 6/2011 |
| EP | 2172240 B1 | 12/2012 |
| EP | 2338411 B1 | 11/2013 |
| JP | 8243168 A | 9/1996 |
| JP | 2000126301 A | 5/2000 |
| JP | 2000508224 A | 7/2000 |
| JP | 2005040215 | 2/2005 |
| JP | 2005237964 A | 9/2005 |
| JP | 2005345215 A | 12/2005 |
| JP | 2006064465 A | 3/2006 |
| JP | 2006255401 A | 9/2006 |
| JP | 2007181696 A | 7/2007 |
| WO | WO 94/17856 A1 | 8/1994 |
| WO | WO 95/10326 A | 4/1995 |
| WO | WO 96/05768 | 2/1996 |
| WO | WO 97/29678 A | 8/1997 |
| WO | WO 97/29709 A | 8/1997 |
| WO | WO 97/29710 A | 8/1997 |
| WO | WO 98/29032 A | 7/1998 |
| WO | WO 03/020139 A | 3/2003 |
| WO | WO 2006/043884 A1 | 4/2006 |
| WO | WO 2006/086152 A | 8/2006 |
| WO | WO 2006/092563 A | 9/2006 |
| WO | WO 2006/135483 A2 | 12/2006 |
| WO | WO 2007/015139 A2 | 2/2007 |
| WO | WO 2007/025230 A | 3/2007 |
| WO | WO 2007/050960 A | 5/2007 |
| WO | WO 2007/067938 | 6/2007 |
| WO | WO 2007/076312 A2 | 7/2007 |
| WO | WO 2007/082216 A | 7/2007 |
| WO | WO 2007/098494 A1 | 8/2007 |
| WO | WO 2007/111182 A | 10/2007 |
| WO | WO 2008/053402 A1 | 5/2008 |
| WO | WO 2008/147599 A1 | 12/2008 |
| WO | WO 2009/065140 A1 | 5/2009 |
| WO | WO 2009/078280 A | 6/2009 |
| WO | WO 2009/085470 A | 7/2009 |
| WO | WO 2009/147399 A | 12/2009 |
| WO | WO 2010/008975 A | 1/2010 |
| WO | WO 2011/046874 A1 | 4/2011 |

OTHER PUBLICATIONS

Okumura Y. et al., "A Systematic Analysis of in Vivo Contact Forces on Virtual Catheter Tip / Tissue Surface Contact During Cardiac Mapping and Intervention"; J Cardiovasc Electrophysiol, vol. 19, No. 6, pp. 632-640, Jun. 2008.

U.S. Appl. No. 11/868,733, filed Oct. 8, 2007.

U.S. Appl. No. 12/134,592, filed Jun. 6, 2008.

U.S. Appl. No. 12/327,226, filed Dec. 3, 2008.

EP Partial Search Report No. EP 09 25 2879 Dated Mar. 18, 2010.

Biter, William J. et al., "Magnetic Wire Strain Sensor", 33rd International Sampe Technical Conference, Nov. 5-8, 2001, vol. 33, pp. 12-23, Seattle, WA.

Biter, William J. et al., "Magnetic Wire for Monitoring Strain in Composites", *Sensors,* Jun. 2001, www.sensormag.com, pp. 110-114.

Guo, Shuxiang et al., "Control and Experimental results of a Catheter Operating System", Feb. 21-26, 2009, Proceedings of the 2008 IEEE, International Conference on Robotics and Biomimetics, Bankok, Thailand, pp. 91-95.

Instron Marketing Brochure, "Medical Device Testing Systems", Instron 2007 http://web.archive.org/web/20080318092822 /http://www.instron.com.tr/wa/library/streamfile.aspx?doc=1678&download=true.

Instron, "Series 3300 Load Frames, Reference Manual Equipment", Instron, pp. 1-5 and 1-10, 2004.

Peirs, J. et al., "Design of an Optical Force Sensor for Force Feedback during Minimally Invasive Robotic Surgery", Eurosensors XVII,

(56) References Cited

OTHER PUBLICATIONS 2003, pp. 1063-1066, http://mech.kuleuven.be/micro/pub/medic/Paper_Eurosensors_2003_MIS_sensorextended.pdf.
Partial European Search Report mailed on Sep. 18, 2009 from related European Patent Application No. 08253265.6.
Partial European Search Report mailed on Dec. 7, 2009 from related European Patent Application No. 09251502.2.
European Search Report mailed on Mar. 8, 2010 from related European Patent Application No. 09252143.4.
Partial European Search Report mailed on Apr. 1, 2010 from related European Patent Application No. 09252721.7.
European Search Report mailed on Mar. 2, 2011 from related European Patent Application No. 10175931.4.
European Search Report mailed on Mar. 28, 2011 from related European Patent Application No. 10252189.5.
European Search Report mailed on Mar. 28, 2011 from related European Patent Application No. 10252191.1.
European Search Report mailed on Mar. 30, 2011 from related European Patent Application No. 10252020.2.
European Search Report mailed on May 16, 2011 from related European Patent Application No. 10252232.3.
European Search Report mailed on Aug. 5, 2011 from related European Patent Application No. 11158804.2.
European Search Report mailed on Sep. 20, 2011 from related European Patent Application No. 11250066.5.
European Search Report mailed on Sep. 23, 2011 from related European Patent Application No. 11169251.3.
European Search Report mailed on Oct. 28, 2011 from related European Patent Application No. 11171842.5.
European Search Report mailed on Nov. 17, 2011 from related European Patent Application No. 11177600.1.
European Search Report mailed on Feb. 15, 2012 from related European Patent Application No. 11182854.7.
European Search Report mailed on May 2, 2012 from related European Patent Application No. 11189326.9.
European Search Report mailed on Jun. 4, 2012 from related European Patent Application No. 12163784.7.
European Search Report mailed on Jul. 20, 2012 from related European Patent Application No. 12161784.9.
European Search Report mailed on Nov. 20, 2012 from related European Patent Application No. 12176163.9.
European Search Report mailed on Feb. 11, 2013 from related European Patent Application No. 11187525.8.
European Search Report mailed on Apr. 9, 2013 from related European Patent Application No. 13150145.4.

\* cited by examiner

CATHETER DISPLAY SHOWING TIP ANGLE AND PRESSURE

FIELD OF THE INVENTION

The present invention relates generally to invasive medical devices, and specifically to methods and devices for displaying characteristics of a probe, such as a catheter, inside the body of a patient.

BACKGROUND OF THE INVENTION

In some diagnostic and therapeutic techniques, a catheter is inserted into a chamber of the heart and brought into contact with the inner heart wall. In such procedures, it is generally important that the distal tip of the catheter engages the endocardium with sufficient pressure to ensure good contact. Excessive pressure, however, may cause undesired damage to the heart tissue and even perforation of the heart wall.

For example, in intracardiac radio-frequency (RF) ablation, a catheter having an electrode at its distal tip is inserted through the patient's vascular system into a chamber of the heart. The electrode is brought into contact with a site (or sites) on the endocardium, and RF energy is applied through the catheter to the electrode in order to ablate the heart tissue at the site. Proper contact between the electrode and the endocardium during ablation is necessary in order to achieve the desired therapeutic effect without excessive damage to the tissue.

A number of patent publications describe catheters with integrated pressure sensors for sensing tissue contact. As one example, U.S. Patent Application Publication 2007/0100332, whose disclosure is incorporated herein by reference, describes systems and methods for assessing electrode-tissue contact for tissue ablation. An electro-mechanical sensor within the catheter shaft generates electrical signals corresponding to the amount of movement of the electrode within a distal portion of the catheter shaft. An output device receives the electrical signals for assessing a level of contact between the electrode and a tissue.

As another example, U.S. Pat. No. 6,695,808, whose disclosure is incorporated herein by reference, describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

Other catheters with pressure sensors are described in U.S. Pat. No. 6,241,724 and U.S. Pat. No. 6,915,149, whose disclosures are incorporated herein by reference.

PCT International Publication WO 2007/067938, whose disclosure is incorporated herein by reference, describes a method for displaying catheter electrode-tissue contact in an electro-anatomic mapping and navigation system. The system provides an indication to the physician concerning the electrical coupling of an electrode, such as an ablative or mapping electrode, with a patient. The indication may be provided by changing the color or other display characteristics of the electrode on the navigation system display or by way of providing a waveform indicating the electrode coupling. This manner of providing electrode coupling information is said to minimize physician distraction.

SUMMARY OF THE INVENTION

The embodiments of the present invention that are described hereinbelow provide novel means and methods for displaying parameters associated with the quality of engagement between an invasive probe and tissue within the body of a subject. This sort of display can assist the operator of the probe in visualizing the situation of the probe and thus in ensuring the effectiveness and safety of diagnostic and/or therapeutic procedures that are performed using the probe.

An embodiment of the present invention provides a method for displaying information. The method includes receiving a measurement with respect to an invasive probe inside a body of a subject of at least one probe parameter, selected from a group of parameters consisting of a bend angle of the probe and a pressure on the probe. Responsively to the measurement, an icon is displayed on a display screen representing the at least one probe parameter for viewing by an operator of the probe.

In some embodiments, the probe includes a distal tip that bends at a resilient joint, and receiving the measurement includes measuring a deformation of the joint due to engagement of tissue in the body by the distal tip. In a disclosed embodiment, the probe includes a catheter, which is inserted into a chamber of a heart of the subject and engages myocardial tissue. The method may include applying energy via the distal tip so as to ablate the myocardial tissue, wherein the operator controls application of the energy responsively to the icon. Additionally or alternatively, measuring the deformation includes sensing both the deformation of the joint and a position of the probe within the body by transmitting and receiving one or more magnetic fields.

Typically, displaying the icon includes positioning the icon on the display screen so as to represent a location of the probe within the body. Positioning the icon may include locating the icon on the display screen relative to a map of a surface of an organ of the body, and wherein receiving the measurement includes measuring the pressure between the probe and the surface.

In a disclosed embodiment, displaying the icon includes presenting the icon so as to show both the bend angle and the pressure, wherein the icon is articulated to show the bend angle and is colored to represent the pressure.

There is also provided, in accordance with an embodiment of the present invention, apparatus for performing a medical procedure, including a display screen arranged for viewing by an operator of an invasive probe inside a body of a subject. A processor is coupled to receive a measurement with respect to the invasive probe of at least one probe parameter, selected from a group of parameters consisting of a bend angle of the probe and a pressure on the probe, and to display an icon on the display screen, responsively to the measurement, representing the at least one probe parameter.

There is additionally provided, in accordance with an embodiment of the present invention, a computer software product, including a computer-readable medium in which program instructions are stored, which instructions, when read by a computer, cause the computer to receive a measurement with respect to an invasive probe inside a body of a subject of at least one probe parameter, selected from a group of parameters consisting of a bend angle of the probe and a pressure on the probe, and to display, responsively to the measurement, an icon on a display screen representing the at least one probe parameter for viewing by an operator of the probe.

The present invention will be more fully understood from the following detailed description of the embodiments thereof, taken together with the drawings in which:

DETAILED DESCRIPTION OF THE INVENTION

Figure 1:
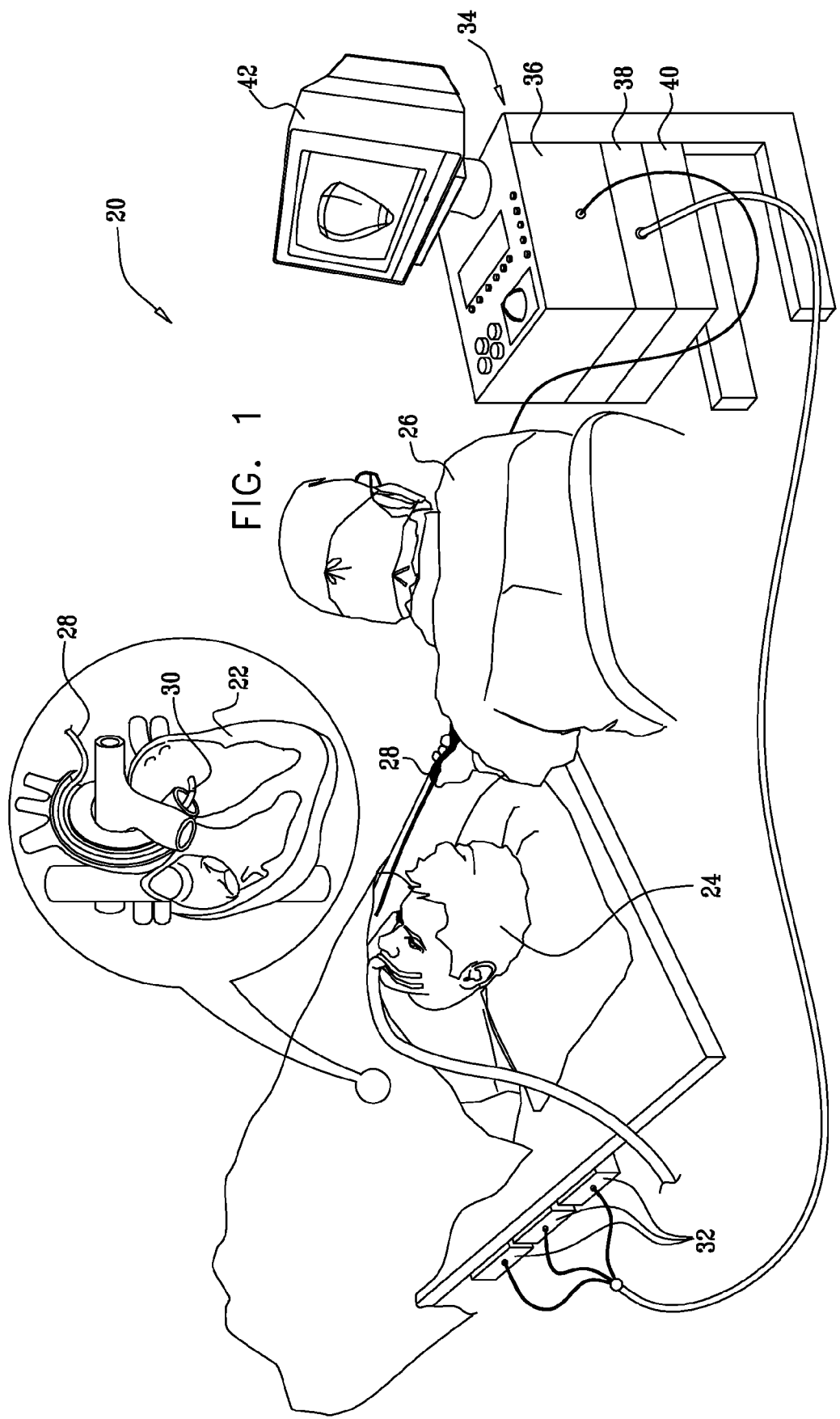
FIG. 1 is a schematic, pictorial illustration of a catheter-based medical system, in accordance with an embodiment of the present invention.

FIG. 1 is a schematic, pictorial illustration of a system 20 for cardiac catheterization, in accordance with an embodiment of the present invention. System 20 may be based, for example, on the CARTO® system, produced by Biosense Webster Inc. (Diamond Bar, Calif.). This system comprises an invasive probe in the form of a catheter 28 and a control console 34. In the embodiment described hereinbelow, it is assumed that catheter 28 is used in ablating endocardial tissue, as is known in the art. Alternatively, the catheter may be used mutatis mutandis, for other therapeutic and/or diagnostic purposes in the heart or in other body organs.

An operator 26, such as a cardiologist, inserts catheter 28 through the vascular system of a patient 24 so that a distal end 30 of the catheter enters a chamber of the patient's heart 22. The operator advances the catheter so that the distal tip of the catheter engages endocardial tissue at a desired location or locations. Catheter 28 is typically connected by a suitable connector at its proximal end to console 34. The console comprises a radio frequency (RF) generator 40, which supplies high-frequency electrical energy via the catheter for ablating tissue in the heart at the locations engaged by the distal tip, as described further hereinbelow. Alternatively, the catheter and system may be configured to perform ablation by other techniques that are known in the art, such as cryo-ablation. Further alternatively or additionally, the catheter and system may be used to perform other sorts of therapeutic and/or diagnostic procedures, such as electro-anatomical mapping.

Console 34 uses a position sensing technique to determine position coordinates of distal end 30 of catheter 28 inside heart 22. In the present embodiment, it is assumed that the console uses magnetic position sensing, which is also used in deriving angle and pressure information with respect to the distal end, as described further hereinbelow. Alternatively or additionally, the principles of the present invention may be applied using other position sensing and pressure sensing techniques, as are known in the art.

For the purpose of magnetic position sensing, a driver circuit 38 in console 34 drives field generators 32 to generate magnetic fields within the body of patient 24. Typically, the field generators comprise coils, which are placed below the patient's torso at known positions external to the patient. These coils generate magnetic fields in a predefined working volume that contains heart 22. A magnetic field sensor within distal end 30 of catheter 28 (not shown in the figures) generates electrical signals in response to these magnetic fields. A signal processor 36 processes these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 36 typically comprises a general-purpose computer, with suitable front end and interface circuits for receiving signals from catheter 28 and controlling the other components of console 34. The processor may be programmed in software to carry out the functions that are described herein. The software may be downloaded to console 34 in electronic form, over a network, for example, or it may be provided on tangible media, such as optical, magnetic or electronic memory media. Alternatively, some or all of the functions of processor 36 may be carried out by dedicated or programmable digital hardware components.

Based on the signals received from catheter 28 and other components of system 20, processor 36 drives a display 42 to give operator 26 visual feedback regarding distal end 30 of catheter 28 in the patient's body, as well as status information and guidance regarding the procedure that is in progress. The visual feedback shows the pressure on the distal end, as well as the bend angle of the distal tip of the catheter, as is described further hereinbelow with reference to FIG. 3.

Alternatively or additionally, system 20 may comprise an automated mechanism for maneuvering and operating catheter 28 within the body of patient 24. Such mechanisms are typically capable of controlling both the longitudinal motion (advance/retract) of the catheter and transverse motion (deflection/steering) of the distal end of the catheter. Some mechanisms of this sort use DC magnetic fields for this purpose, for example. In such embodiments, processor 36 generates a control input for controlling the motion of the catheter based on the signals provided by the magnetic field sensor in the catheter. As noted earlier, these signals are indicative of both the position of the distal end of the catheter and force exerted on the distal end. In this case, the pressure and bend angle shown on display 42 may be used by a human operator in monitoring the status and progress of the automated procedure.

Figure 2:
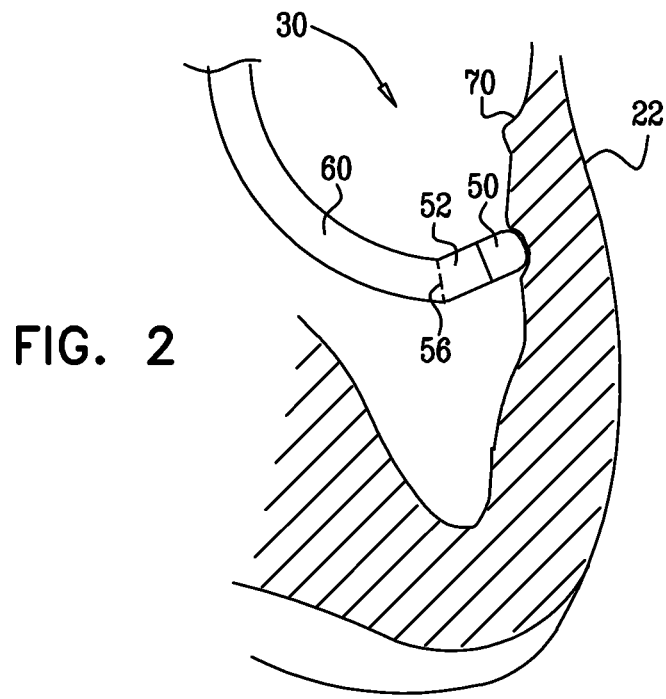
FIG. 2 is a schematic detail view showing the distal tip of a catheter in contact with endocardial tissue, in accordance with an embodiment of the present invention.

FIG. 2 is a schematic sectional view of a chamber of a heart 22, showing distal end 30 of catheter 28 inside the heart, in accordance with an embodiment of the present invention. The catheter comprises an insertion tube 60, which is typically inserted into the heart percutaneously through a blood vessel, such as the vena cava or the aorta. An electrode 50 on a distal tip 52 of the catheter engages endocardial tissue 70. Pressure exerted by the distal tip against the endocardium deforms the endocardial tissue locally, so that electrode 50 contacts the tissue over a relatively large area. In the pictured example, the electrode engages the endocardium at an angle, rather than head-on. Distal tip 52 therefore bends at a resilient joint 56 relative to the distal end of insertion tube 60 of the catheter. The bend may facilitate optimal contact between the electrode and the endocardial tissue.

Because of the elastic quality of joint 56, the angle of bending and the axial displacement of the joint are proportional to the pressure exerted by tissue 70 on distal tip 52 (or equivalently, the pressure exerted by the distal tip on the tissue). Measurement of the deformation of the joint, in terms of bend angle and axial displacement, thus gives an indication of this pressure. The pressure indication may be used by operator 26 of system 20 in ensuring that the distal tip is pressing against the endocardium firmly enough to give the desired therapeutic or diagnostic result, but not so hard as to cause undesired tissue damage.

Various techniques may be used in measuring the bend angle and pressure exerted on distal tip 52. Components and methods that may be used for this purpose are described, for example, in U.S. patent application Ser. No. 11/868,733, filed Oct. 8, 2007, which is assigned to the assignee of the present patent application and whose disclosure is incorporated herein by reference. This patent application describes a catheter whose distal tip is coupled to the distal end of the catheter insertion tube by a spring-loaded joint (such as joint 56), which deforms in response to pressure exerted on the distal tip when it engages tissue. A magnetic position sensing assembly within the probe, comprising coils on opposite sides of the joint, senses the position of the distal tip relative to the distal end of the insertion tube. Changes in this relative position are indicative of deformation of the spring and thus give an indication of the pressure.

Joint 56 may comprise a superelastic coupling member, as described in U.S. patent application Ser. No. 12/134,592, filed Jun. 6, 2008. Alternatively, the coupling member may comprise a coil spring or any other suitable sort of resilient component with the desired flexibility and strength characteristics. U.S. patent application Ser. No. 12/327,226, filed Dec. 3, 2008, describes an arrangement of magnetic coils within the distal end of the catheter that can be used in sensing the tip angle and pressure with enhanced accuracy. Both of these two patent applications are assigned to the assignee of the present patent application, and their disclosures are incorporated herein by reference.

Figure 3:
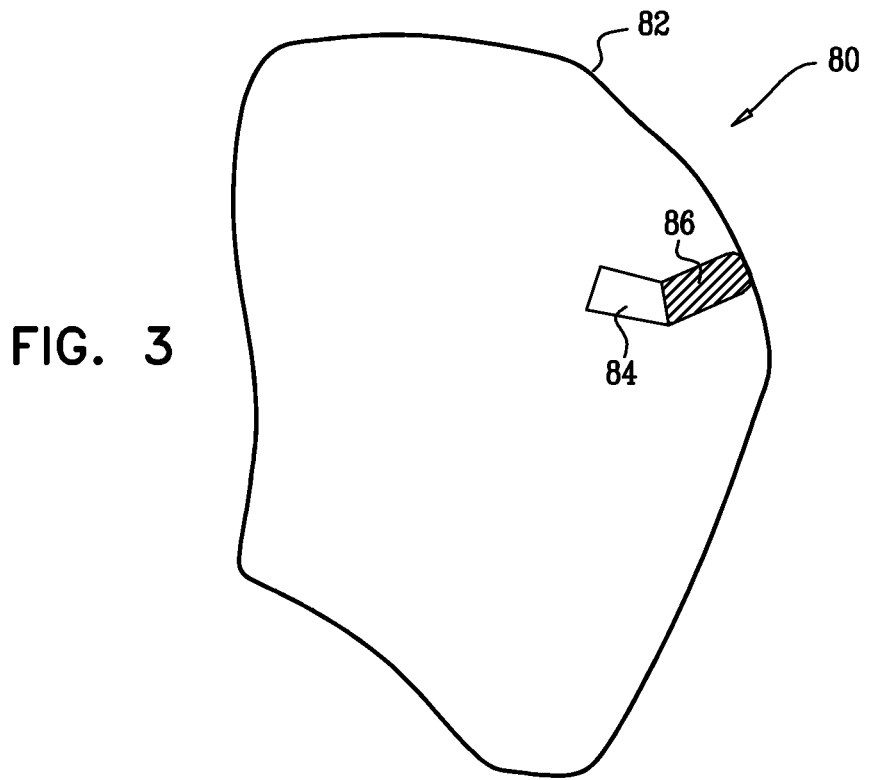
FIG. 3 is a schematic representation of a display screen including an icon corresponding to a catheter tip, in accordance with an embodiment of the present invention.

FIG. 3 is a schematic representation of a map 80 of a heart chamber, which includes an icon 84 corresponding to distal end 30 of catheter 28, in accordance with an embodiment of the present invention. A map of this sort is typically presented on display 42, as an aid to operator 26 in visualizing the distal end of the catheter within heart 22. The map includes a graphical representation of an inner surface 82 of the heart chamber in which the distal end of the catheter is located. (Surface 82 may be fully reconstructed, as shown in FIG. 3, or only partially reconstructed.) The position of icon 84 relative to surface 82 gives the operator an indication of the location of the actual distal end of the catheter in the heart chamber.

Icon 84 shows not only the location of distal end 30, but also angular and pressure characteristics. In the example shown in FIG. 3, the icon is articulated to show the measured bend angle of distal tip 52 relative to insertion tube 60. If the operator sees that the distal tip of the catheter is sharply bent, for example, he or she may readjust the position of the catheter before continuing with a diagnostic or therapeutic procedure, such as ablating the heart tissue.

Furthermore, at least a portion 86 of the icon may be colored (represented in the figure by hatching) to indicate the pressure. For example, green coloring may indicate that the pressure is within the correct pressure range for RF ablation, while red indicates too much pressure, and blue indicates too little. The pressure ranges may be preset, or they may be adjusted by the operator. In either case, the operator will then apply the RF energy only when the pressure is within the range that will give the desired therapeutic result.

The graphical display of pressure and bend angle by icon 84 gives the operator additional visual information that is not provided by display techniques that are known in the art. This additional information can be useful as a complement to or in place of measurement of electrode/tissue electrical contact resistance. The pressure and/or angle display itself is important, for example, under the following circumstances:

When touching scarred myocardium, the electrical contact resistance will not accurately reflect pressure, and therefore direct pressure measurement is needed.

When the catheter touches the heart wall sideways (along the length of the catheter), the electrical contact resistance may be low, because the contact area is large, even though the pressure exerted by the catheter on the heart wall is low. The pressure and/or angle display of FIG. 3 allows the operator to detect and rectify this sort of situation.

Similarly, when a catheter touches a trabeculated wall, the electrical contact resistance may be low even if little or no pressure is applied. Direct pressure measurement enables the operator to detect and rectify this sort of situation, as well.

Although icon 84 in FIG. 3 represents both tip angle and pressure parameters, in addition to location of the catheter tip, the examples above show that it can be useful to display either the angle or the pressure by itself. Alternatively or additionally, one or both of the angle and pressure measurements may be displayed together with a measurement of electrical contact resistance or other parameters. Furthermore, although FIG. 3 shows a particular mode of graphical representation, other techniques for displaying angle and pressure data will be apparent to those skilled in the art and are considered to be within the scope of the present invention. The display techniques that are described or suggested hereinabove may be used not only in cardiac catheterization procedures, but also in other types of invasive diagnostic and therapeutic applications.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for displaying information, comprising:
receiving a measurement with respect to an invasive probe comprising an insertion tube inside a body of a subject of at least one probe parameter, selected from a group of parameters consisting of a bend angle of the probe and a pressure on the probe, wherein the probe further comprises a resilient joint at a distal end of the insertion tube and a distal tip, wherein the resilient joint comprises a spring-loaded joint configured to permit axial displacement and angular deflection of the distal tip, and wherein the distal tip is configured to bend at the spring-loaded joint, and a magnetic position sensing assembly located within the probe comprising coils on opposite sides of the spring-loaded joint and wherein receiving the measurement comprises measuring the axial displacement and angular deflection of the distal tip due to engagement of tissue in the body by the distal tip by using the magnetic position sensing assembly to sense the position of the distal tip relative to the distal end of the insertion tube; and
responsively to the measurement, displaying an icon on a display screen representing the at least one probe parameter for viewing by an operator of the probe, wherein displaying the icon shows both the bend angle and the pressure, the pressure being an indication and in proportion of both the axial displacement and angular deflection of the distal tip, and wherein the icon is articulated to show the bend angle and is colored to represent whether the pressure is within a pre-determined pressure range.

2. The method according to claim 1, wherein the probe further comprises a catheter, which is inserted into a chamber of a heart of the subject and engages myocardial tissue.

3. The method according to claim 2, further comprising applying energy via the distal tip so as to ablate the myocardial tissue, wherein the operator controls application of the energy responsively to the icon.

4. The method according to claim 1, wherein measuring the deformation further comprises sensing both the deformation of the joint and a position of the probe within the body by transmitting and receiving one or more magnetic fields.

5. The method according to claim 1, wherein displaying the icon further comprises positioning the icon on the display screen so as to represent a location of the probe within the body.

6. The method according to claim 5, wherein positioning the icon further comprises locating the icon on the display screen relative to a map of a surface of an organ of the body, and wherein receiving the measurement comprises measuring the pressure between the probe and the surface.

7. An apparatus for performing a medical procedure, comprising:
   invasive probe comprising an insertion tube, a resilient joint at a distal end of the insertion tube, and a distal tip, wherein the resilient joint comprises a spring-loaded joint that is configured to permit axial displacement and angular deflection of the distal tip, the probe further comprising a magnetic position sensing assembly located within the probe comprising coils on opposite sides of the spring-loaded joint;
   a display screen arranged for viewing by an operator of the invasive probe inside a body of a subject; and
   a processor, which is coupled to receive a measurement with respect to the invasive probe of at least one probe parameter, selected from a group of parameters consisting of a bend angle of the probe and a pressure on the probe, the processor being configured to measure the axial displacement and angular deflection of the distal tip due to engagement of tissue in the body by the distal tip by using the magnetic position sensing assembly to sense the position of the distal tip relative to the distal end of the insertion tube and to display an icon on the display screen, responsively to the measurement, representing the at least one probe parameter, wherein the icon shows both the bend angle and the pressure, the pressure being an indication and in proportion of both the angular and axial deformation of the spring-loaded joint, and wherein the icon is articulated to show the bend angle and is colored to represent whether the pressure is within a pre-determined pressure range.

8. The apparatus according to claim 7, wherein the probe further comprises a catheter, for insertion into a chamber of a heart of the subject so as to engage myocardial tissue.

9. The apparatus according to claim 8, wherein the catheter is configured to apply energy via the distal tip so as to ablate the myocardial tissue, wherein the operator controls application of the energy responsively to the icon.

10. The apparatus according to claim 7, further comprising at least one magnetic field generator for generating a magnetic field in a vicinity of the probe, wherein the processor is configured to measure both the deformation of the joint and a position of the probe within the body responsively to the magnetic field.

11. The apparatus according to claim 7, wherein the processor is configured to position the icon on the display screen so as to represent a location of the probe within the body.

12. The apparatus according to claim 11, wherein the processor is configured to generate a map of a surface of an organ of the body, to locate the icon on the display screen relative to the map, and to measure the pressure between the probe and the surface.

* * * * *